(12) United States Patent
Vilermo et al.

(10) Patent No.: US 10,213,155 B2
(45) Date of Patent: Feb. 26, 2019

(54) METHOD AND APPARATUS FOR PROCESSING USER LACTATE LEVEL INFORMATION

(71) Applicant: Nokia Technologies Oy, Espoo (FI)

(72) Inventors: Miikka Vilermo, Siuro (FI); Jussi Leppänen, Tampere (FI); Lasse Laaksonen, Tampere (FI); Pasi Saari, Jyväskylä (FI)

(73) Assignee: Nokia Technologies Oy, Espoo (FI)

( * ) Notice: Subject to any disclaimer, the term of this patent is extended or adjusted under 35 U.S.C. 154(b) by 437 days.

(21) Appl. No.: 14/972,439

(22) Filed: Dec. 17, 2015

(65) Prior Publication Data

US 2016/0174891 A1   Jun. 23, 2016

(30) Foreign Application Priority Data

Dec. 23, 2014 (EP) .................... 14200039

(51) Int. Cl.
*A61B 5/00* (2006.01)
*A61B 5/11* (2006.01)
*A61B 5/145* (2006.01)
*G06F 19/00* (2018.01)

(52) U.S. Cl.
CPC ............ *A61B 5/486* (2013.01); *A61B 5/002* (2013.01); *A61B 5/1118* (2013.01); *A61B 5/14546* (2013.01); *A61B 5/4519* (2013.01); *A61B 5/6801* (2013.01); *A61B 5/7415* (2013.01); *G06F 19/3481* (2013.01)

(58) Field of Classification Search
CPC .................................... A61B 5/486
USPC ........................................... 702/19
See application file for complete search history.

(56) References Cited

U.S. PATENT DOCUMENTS

2006/0004265 A1   1/2006  Pulkkinen et al.
2015/0359480 A1*  12/2015 Guthrie .............. A61B 5/14546
                                                    600/301

FOREIGN PATENT DOCUMENTS

CN    101980228 A    2/2011
CN    103316466 A    9/2013

OTHER PUBLICATIONS

Jia et al., "Electrochemical Tattoo Biosensors for Real-Time Non-invasive Lactate Monitoring in Human Perspiration" Analytical Chemistry (2013) vol. 85, pp. 6553-6560 (Year: 2013).*

* cited by examiner

Primary Examiner — Jerry Lin
(74) Attorney, Agent, or Firm — Harrington & Smith

(57) ABSTRACT

A method and apparatus for receiving, from a wearable sensor, current lactate level information of a user; setting, by the user, a target fatigue value; determining target lactate level information based on the target fatigue value; receiving characteristics of a physical exercise including information of an end of the physical exercise; determining adjusted characteristics of the physical exercise in order to match the current user lactate level information in the end of the physical exercise with the target lactate level information, based on the current lactate level information of the user, the target lactate level information and the characteristics for the physical exercise; and providing feedback to the user based on the adjusted characteristics of the physical exercise.

15 Claims, 5 Drawing Sheets

METHOD AND APPARATUS FOR PROCESSING USER LACTATE LEVEL INFORMATION

TECHNICAL FIELD

The present application generally relates to providing non-invasive biometric information of a user, especially lactate level information, and an apparatus for providing physical exercise feedback for the user based on the lactate level information.

BACKGROUND

This section illustrates useful background information without admission of any technique described herein representative of the state of the art.

Biometric non-invasive information is used more and more in today's user devices. Biometric information may provide information on a change in a physiological state of a user's body, even in real-time, based on various biometric signals collected from the body and providing an appropriate information to the user, thereby allowing the user to improved control and awareness.

One example of such biometric information is a heart rate (HR) that is a cardiovascular index that is most prominently observed when people train or exercise. The HR can be measured using various methods. Usually, the HR is measured by counting the number of pulses per unit time using an electrocardiogram signal or a photoplethysmography (PPG) signal. The HR is the number of heartbeats per minute and is expressed in beats per minute (BPM).

Various training techniques may be developed for effective self-control learning using biometric information technique in which a user's HR is measured and reported to the user and an appropriate signal is provided to the user when the user's HR reaches a predetermined target value.

However, pedometers and heart rate monitors can give only an estimate of the user's current physiological condition and even for that they require that the user has given his personal aerobic and anaerobic limits to the user device processing the information. Very often exercises are based on the idea of a constant heart rate during the physical exercise. A constant heart rate makes predicting the future, and the point where the user reaches a certain exhaustion level, impossible from the heart rate. For example, if the physical exercise is such that in the beginning user heart rate is 130, in the end of the exercise still being 130, wherein the user is in the beginning in good shape and in the end really tired, it is clear that a heart rate alone is not sufficient to make predictions about the physical shape of the user. Thus, there is a need for an improved method and apparatus to more accurately estimating of the user physiological condition and improving the user assistance for physical exercises.

SUMMARY

Various aspects of examples of the invention are set out in the claims.

According to a first example aspect of the present invention, there is provided a method, comprising:

receiving, from a wearable sensor, current lactate level information of a user;

setting, by the user, a target fatigue value;

determining target lactate level information based on the target fatigue value;

receiving characteristics of a physical exercise comprising information of an end of the physical exercise;

determining adjusted characteristics of the physical exercise in order to match the current user lactate level information in the end of the physical exercise with the target lactate level information, based on the current lactate level information of the user, the target lactate level information and the characteristics for the physical exercise; and providing feedback to the user based on the adjusted characteristics of the physical exercise.

In an embodiment, the method comprises receiving setting from the user, for a target fatigue value.

In an embodiment, the information of an end of the physical exercise may comprise an end time. The adjusted characteristics of the physical exercise may comprise an adjusted speed for the physical exercise. The feedback to the user may comprise instructions to change exercise speed based on the adjusted speed.

In an embodiment, the method further comprises:

receiving characteristics of a physical exercise comprising information of a start time, a start location and an end location of the physical exercise;

defining a time-scale for lactate level information, wherein lactate levels gradually rising from the current lactate level to a target lactate level, and the time-scale length determined based on the start and the end time of the physical exercise;

estimating a distance covered by the user during the physical exercise to match the time-scale;

determining route information between the start location and the end location based on the estimated distance; and providing feedback to the user comprising instructions based on the route information.

In an embodiment, the method further comprises:

dynamically estimating a distance covered by the user during the physical exercise to match the time-scale;

updating route information between the start location and the end location based on the estimated distance; and providing feedback to the user comprising instructions based on the updated route information.

In an embodiment, the method further comprises:

comparing the current lactate level information to the defined time-scale for lactate level information; and providing feedback comprising a music file with a higher tempo, in response to the current lactate level information being below the defined time-scale for the lactate level information based on the comparison; and providing feedback comprising a music file with a lower tempo, in response to the current lactate level information being above the defined time-scale for the lactate level information based on the comparison.

In an embodiment, the method further comprises:

receiving, from a second wearable sensor, current lactate level information of a second user;

receiving characteristics of a second physical exercise comprising information of an end of the second physical exercise;

determining adjusted characteristics of the second physical exercise, in order to match the current user lactate level information of the second user in the end of the second physical exercise, with the target lactate level information of the first user, based on the current user lactate level information of the second user, the target lactate level information of the first user and the characteristics for the second physical exercise; and providing feedback to the second user based on the adjusted characteristics of the second physical exercise.

In an embodiment, the information of an end of the physical exercise comprises an end location of a predetermined route, the adjusted characteristics of the physical exercise comprises an adjusted speed for the physical exercise following the predetermined route, and the feedback to the user comprises instructions to change exercise speed based on the adjusted speed, and the method further comprises:

determining an estimate of a remaining duration of the physical exercise based on the end location of the predetermined route and the adjusted speed; and selecting a music file of duration similar to the remaining duration of the physical exercise.

In an embodiment, the physical exercise comprises at least one of the following: walking; jogging; running; cross-country skiing; skating; swimming; and cycling.

In an embodiment, the method further comprises:

monitoring, during the physical exercise, user lactate level information and a user speed; and defining, using the monitored user lactate level information and the user speed, a model of the user lactate level information as a function of the speed.

In an embodiment, the model being a polynomial regression model, and the method further comprises:

monitoring user lactate level information and a user speed during pre-determined time periods;

determining average speed and user lactate level increase for the time periods;

defining the polynomial regression model having a polynomial order of two, using the average speed and the user lactate level increase for the time periods;

determining an estimate of a remaining duration of the physical exercise based on the end location of the predetermined route and the adjusted speed; and selecting a music file of duration similar to the remaining duration of the physical exercise.

In an embodiment, the method further comprises:

maintaining history data of earlier monitored user lactate level information and user speeds; and defining, using the history data, a model of the user lactate level information as a function of the speed.

According to a second example aspect of the present invention, there is provided an apparatus comprising:

a user interface for transceiving information with a user;

at least one memory including computer program code; the at least one memory and the computer program code configured to, with the at least one processor, cause the apparatus to:

receive current lactate level information of a user;

set, by the user, a target fatigue value;

determine target lactate level information based on the target fatigue value;

receive characteristics of a physical exercise comprising information of an end of the physical exercise;

determine adjusted characteristics of the physical exercise in order to match the current user lactate level information in the end of the physical exercise, with the target lactate level information, based on the current lactate level information of the user, the target lactate level information and the characteristics for the physical exercise; and provide feedback to the user based on the adjusted characteristics of the physical exercise.

In an embodiment, the apparatus further comprises the wearable sensor, wherein the apparatus is a user wearable apparatus.

In an embodiment, the apparatus further comprises:

a communication interface for receiving biometric non-invasive information from a wearable sensor, wherein the at least one memory and the computer program code further configured to, with the at least one processor, cause the apparatus to:

process the received biometric non-invasive information to provide current lactate level information of a user.

According to a third example aspect of the present invention there is provided a computer program comprising computer executable program code configured to control an apparatus, when the computer executable program code is executed, to:

receive current lactate level information of a user;

set, by the user, a target fatigue value;

determine target lactate level information based on the target fatigue value;

receive characteristics of a physical exercise comprising information of an end of the physical exercise;

determine adjusted characteristics of the physical exercise, in order to match the current user lactate level information in the end of the physical exercise with the target lactate level information, based on the current lactate level information of the user, the target lactate level information and the characteristics for the physical exercise; and provide feedback to the user based on the adjusted characteristics of the physical exercise.

Different non-binding example aspects and embodiments of the present invention have been illustrated in the foregoing. The embodiments in the foregoing are used merely to explain selected aspects or steps that may be utilized in implementations of the present invention. Some embodiments may be presented only with reference to certain example aspects of the invention. It should be appreciated that corresponding embodiments may apply to other example aspects as well.

BRIEF DESCRIPTION OF THE DRAWINGS

For a more complete understanding of example embodiments of the present invention, reference is now made to the following descriptions taken in connection with the accompanying drawings in which.

DETAILED DESCRIPTION OF THE DRAWINGS

An example embodiment of the present invention and its potential advantages are understood by referring to FIGS. 1 through 8 of the drawings. In this document, like reference signs denote like parts or steps.

Figure 1:
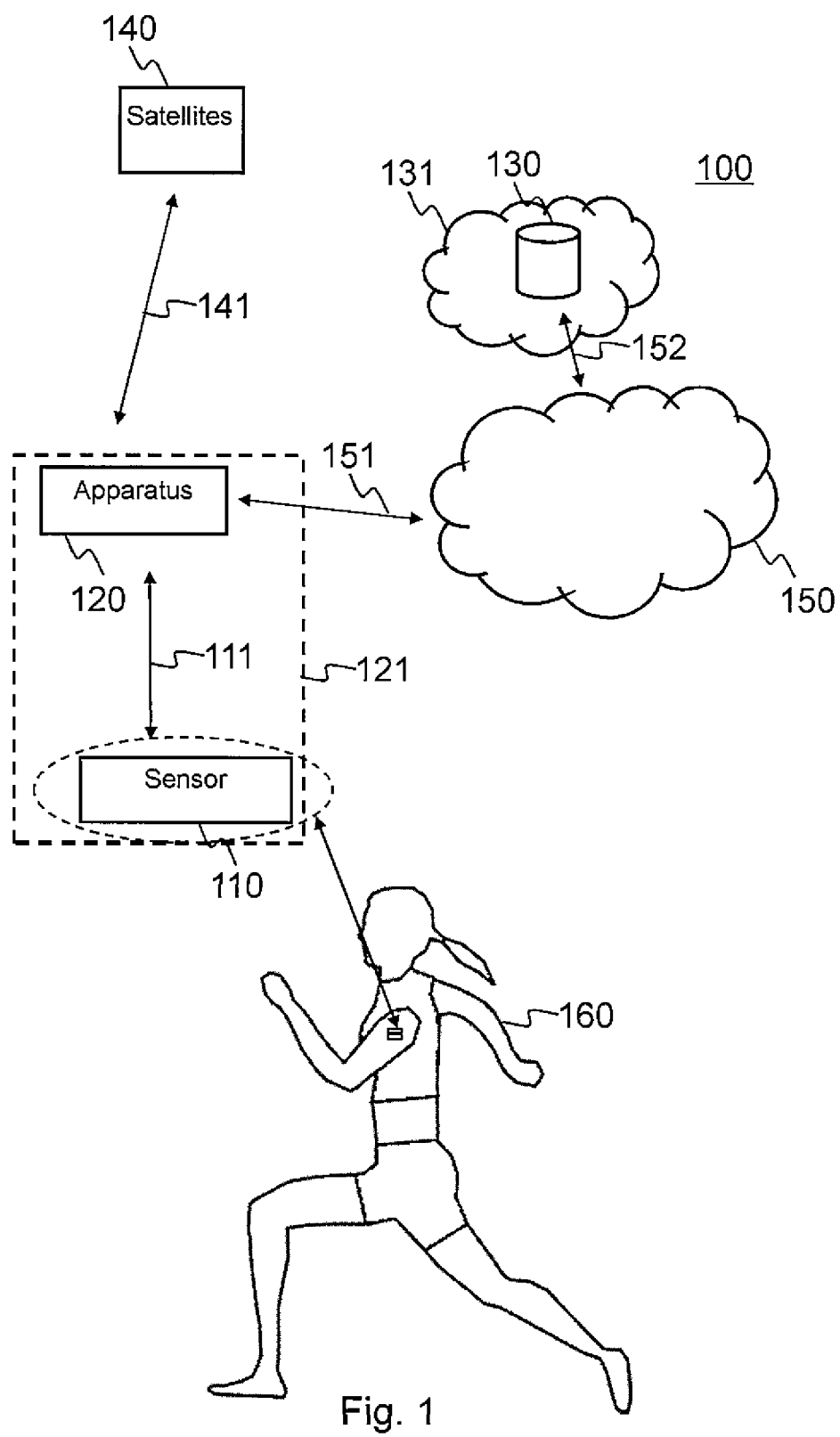
FIG. 1 shows an schematic drawing of a system of an example embodiment.

FIG. 1 shows a schematic drawing of a system 100 of an example embodiment.

At the minimum, the system 100 comprises a user wearable sensor 110 for providing non-invasive biometric information, and an apparatus 120 for receiving and processing the biometric information for user feedback.

In an embodiment, the user wearable sensor 110 and the apparatus 120 may be implemented as separate devices communicating with each other over a local connection 111. The local connection 111 may comprise, for example, at least one of the Bluetooth, Radio Frequency Identification (RF-ID), near field communication (NFC) or other wireless non-cellular connection. The wireless non-cellular connection may comprise industrial, scientific and medical (ISM) radio bands that are radio bands (portions of the radio spectrum) reserved internationally for the use of radio frequency (RF) energy for industrial, scientific and medical purposes, for example. Alternatively, the user wearable sensor 110 may be comprised by the apparatus 120, as illustrated by an integrated apparatus 121. The apparatus 120, 121 may be for example a wrist wearable user apparatus.

In an embodiment, a communication interface module of the apparatus 120 may comprise location modules for tracking location of the portable apparatus 120. Such location modules may comprise a module for providing a connection 141 to satellite based global positioning system (e.g. GPS) 140, a module for cellular based positioning system, a module for wireless non-cellular positioning system (e.g. Wi-Fi) or a module for hybrid positioning system, for example. The positioning system 140 may also be used for user speed detection, altitude detection, route detection and route planning for various embodiments.

In an embodiment, the apparatus 120 may be connected over a wireless or wired connection 151 to a wide area network 150, such as Internet. Router apparatuses (not shown) may be used for providing the access 151 to a wide area network 150. The access 151 may comprise cellular or non-cellular connection.

In an embodiment, the system 100 comprises a server apparatus 130, which comprises a storage device for example for storing and providing user data, service data and subscriber information, over data connection 152. The service data may comprise configuration data, account creation data and measurement data, for example.

In an embodiment, a proprietary application in the apparatus 120 may be a client application of a service whose server application is running on the server apparatus 130 of the system 100. The proprietary application may capture the user input data for the service and provide the user output data, for the service. In an embodiment, information between the apparatus 120 and the system server 130 is transceived via the connections 111, 120, 150, 151, 152 automatically. Thus the user of the apparatus 110 may not need to do any control for the service. The system server 130 may also maintain account creation process details for the service, such as attaching new apparatuses 120 or sensors 110 to the system 100 as well as maintaining synchronized/paired users.

In an embodiment, history data of earlier physical exercises, characteristics of the physical exercises, lactate level information and music file library may be maintained at the server 130.

The server 130 may also provide a cloud service 131 for the portable apparatus 120 data. Optionally, further apparatuses may be added, such as peripheral devices for maintaining, providing or processing the portable apparatus 120 data and communication devices for connecting the peripheral devices to the system 100.

In an embodiment, a wearable sensor 110 may be, for example, a lactate level sensor or a lactate acid level sensor. The wearable sensor 110 may be a lactate level sensor providing lactate level information of the user and based on the lactate level information a lactate acid level is determined.

The sensor 110 operating as a biometric sensor, may be incorporated into textile or clothing of a user, for example.

Alternatively, the sensor 110 operating as a biometric sensor providing user lactate level information may be applied to human skin like a temporary tattoo that can warn users exercising that they are about to become completely exhausted described, the state also described as "bank" or "hit the wall", due to the high lactate level. Thus, stamina and fitness of the user may be monitored.

In an embodiment, the sensor 110 monitors lactate released in sweat. Based on monitored lactate level information lactic acid level may be determined. Lactate is formed when muscles need more energy during a physical exercise than the body can supply from aerobic respiration that suffices during mild exercise. User's body shifts then to anaerobic metabolism, producing lactic acid and lactate. That helps for a while, but lactate builds up in the body, causing extreme fatigue and the state like "banking out" where the user doing the physical exercise just cannot continue. Traditionally measuring lactate has been cumbersome, requiring blood samples or do not giving instant results. However, recently sensors have been developed providing lactate level information using a wearable sensor.

Lactate threshold (LT) (or lactate inflection point (LIP) or anaerobic threshold (AT)) is an exercise intensity at which lactate (more specifically, lactic acid) starts to accumulate in the blood stream. The reason for the acidification of the blood at high exercise intensities is two-fold: the high rates of ATP (adenosine triphosphate) hydrolysis in the muscle release hydrogen ions, as they are co-transported out of the muscle into the blood via the MCT (monocarboxylate transporter), and also bicarbonate stores in the blood begin to be used up. This happens when lactate is produced faster than it can be removed (metabolized) in the muscle. When exercising at or below the LT, any lactate produced by the muscles is removed by the body without it building up.

With higher exercise intensity the lactate level in the blood reaches the anaerobic threshold (AT), or the onset of blood lactate accumulation (OBLA).

The lactate threshold is a useful measure for deciding exercise intensity for training and racing in endurance sports (e.g. long distance running, cycling, rowing, swimming and cross country skiing), but varies between individuals and can be increased with training. Interval training takes advantage of the body being able to temporarily exceed the lactate threshold, and then recover (reduce blood-lactate) while operating below the threshold and while still doing physical activity. Interval training can take the form of many different types of exercise and should closely replicate the movements found in the sport.

Although the lactate threshold may be defined as the point when lactic acid starts to accumulate, some testers approximate this by using the point at which lactate reaches a concentration of 4 mM (mmol/liter). At rest it is around 1 mM.

The lactate sensor 110 may be applied to the skin of a user 160 like a temporary tattoo that stays on and flexes with body movements. The sensor 110 measures lactate levels, for example from user's sweat, during the physical exercise. Such skin-worn metabolite biometric sensor 110 enables useful insights into physical performance and overall physiological status. Sweat lactate levels correlate with fitness, performance and blood lactate levels.

In an embodiment, a biometric sensor 110, such as the lactate sensor, may comprise a bio battery offering certain advantages over conventional batteries: The bio battery recharges more quickly, uses renewable energy sources (in this case, sweat), and are safer because they do not explode or leak toxic chemicals. The sweat-powered bio battery produces energy by passing current, in the form of electrons, from an anode to a cathode. In this case, the anode contained the enzyme that removes electrons from lactate, and the cathode contained a molecule that accepts the electrons.

An apparatus 120 may comprise a user interface or alternatively may not comprise user interface at all but instead the apparatus 120 is remotely operated via an external device (not shown). The apparatus 120 is capable of locally executing software program code. The software program code may be a client application of a service whose server application is running on a server 130 of the system 100.

Figure 2:
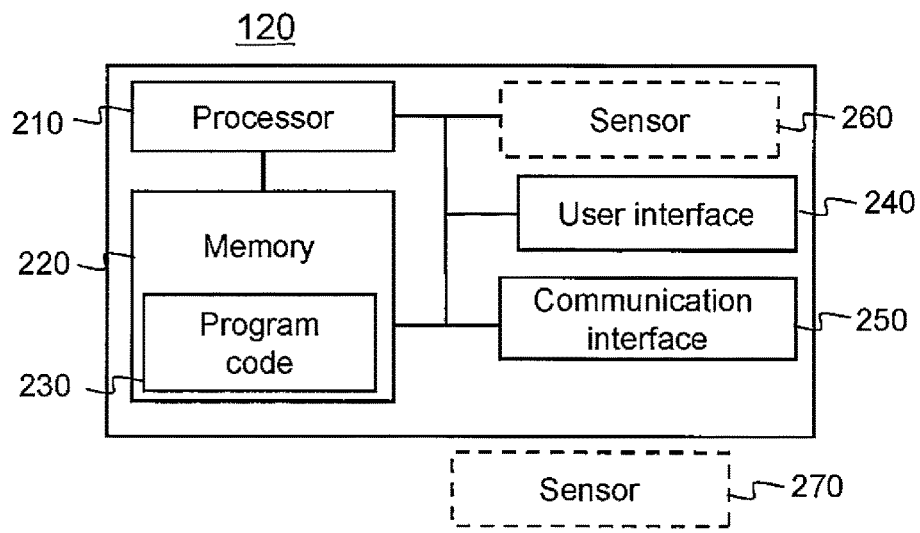
FIG. 2 shows a block diagram of the apparatus of an example embodiment.

FIG. 2 presents an example block diagram of an apparatus 120 in which various embodiments of the invention may be applied. The apparatus 120 may be a portable device, a user wearable device, a wrist wearable device or other similar device. All elements described in FIG. 2 are not necessary to be implemented in the same apparatus 120.

In an embodiment, a sensor 260, 270 may be implemented as a separate device 270 communicating via the communication interface 250 with the apparatus 120, or as an integrated sensor 260 within the apparatus 120. The user interface 240 may be implemented also in another device connected via a communication interface 250 to the apparatus 110. Such device may comprise a mobile phone, a smart phone, or a tablet, for example. In an embodiment, the apparatus 120 may communicate with a plurality of sensors 260, 270, both internal and external sensors, and of a plurality of users.

The general structure of the apparatus 120 comprises a user interface 240, a communication interface 250, a processor 210, and a memory 220 coupled to the processor 210. The apparatus 120 further comprises software 230 stored in the memory 220 and operable to be loaded into and executed in the processor 210. The software 230 may comprise one or more software modules and can be in the form of a computer program product. Not all elements of FIG. 2 are necessary but optional for the portable apparatus 120, such as the user interface 240.

The processor 210 may be, e.g., a central processing unit (CPU), a microprocessor, a digital signal processor (DSP), a graphics processing unit, or the like. FIG. 2 shows one processor 210, but the apparatus 120 may comprise a plurality of processors.

The memory 220 may be for example a non-volatile or a volatile memory, such as a read-only memory (ROM), a programmable read-only memory (PROM), erasable programmable read-only memory (EPROM), a random-access memory (RAM), a flash memory, a data disk, an optical storage, a magnetic storage, a smart card, or the like. The apparatus 120 may comprise a plurality of memories. The memory 220 may be constructed as a part of the apparatus 120 or it may be inserted into a slot, port, or the like of the apparatus 120 by a user. The memory 220 may serve the sole purpose of storing data, or it may be constructed as a part of an apparatus serving other purposes, such as processing data.

The user interface 240 may comprise circuitry for receiving input from a user of the apparatus 120, e.g., via a keyboard, a touchpad, a motion sensor, a touch-screen of the apparatus 120, speech recognition circuitry, gesture recognition circuitry or an accessory device, such as a headset or a remote controller, for example. Furthermore, the user interface 240 may comprise circuitry for providing output for the user via a display, a speaker, a touch-sensitive display or a tactile feedback device, for example.

The communication interface module 250 implements at least part of data transmission. The communication interface module 250 may comprise, e.g., a wireless or a wired interface module. The wireless interface may comprise such as a WLAN, Bluetooth, infrared (IR), radio frequency identification (RF ID), NFC, GSMIGPRS, CDMA, WCDMA, or LTE (Long Term Evolution) radio module. The wired interface may comprise such as universal serial bus (USB), HDMI, SCART or RCA, for example. The communication interface module 250 may be integrated into the apparatus 120, or into an adapter, card or the like that may be inserted into a suitable slot or port of the apparatus 120. The communication interface module 250 may support one radio interface technology or a plurality of technologies. The communication interface module 250 may support one wired interface technology or a plurality of technologies. The apparatus 120 may comprise a plurality of communication interface modules 250.

In an embodiment, the communication interface module 250 may comprise location modules for tracking location of the apparatus 120. Such location modules may comprise a module for satellite based global positioning system (e.g. GPS), a module for cellular based positioning system, a module for wireless non-cellular positioning system (e.g. Wi-Fi) or a module for hybrid positioning system, for example.

In an embodiment, the communication interface 250 with a satellite based global positioning system (e.g. GPS) may detect altitude of the user to provide an estimate of thinness of air. Such estimate of air thinness may be used as a further input for determining adjusted characteristics of the physical exercise in order to match the current user lactate level information in the end of the physical exercise with the target lactate level information.

While the composition of the air stays the same, the expansion means that the air is 'thinner'. At higher altitudes a user inhales less oxygen and nitrogen molecules than she would at sea level and triggering user body to increase its heart rate and respiratory rate to increase the amount of oxygen taken in and circulated around the body. This affects also the lactate levels of the user.

A skilled person appreciates that in addition to the elements shown in FIG. 2, the apparatus 120 may comprise other elements, such as microphones, speakers, sensors, cameras, as well as additional circuitry such as input/output (I/O) circuitry, memory chips, application-specific integrated circuits (ASIC), processing circuitry for specific purposes such as source coding/decoding circuitry, channel coding/decoding circuitry, ciphering/deciphering circuitry, and the like. Additionally, apparatus 120 may comprise a disposable or rechargeable battery (not shown) for powering when external power if external power supply is not available.

In an embodiment, the apparatus 120 comprises an additional sensor 260, 270 for providing metadata associated to the biometric information. The metadata may comprise at least one of the following: temperature information; pressure information; movement information; location information; and humidity information.

In an embodiment, the apparatus 120 comprises speech or gesture recognition means. Using these means, a pre-defined phrase or a gesture may be recognized from the speech or the gesture and translated into control information for the apparatus 120.

In an embodiment, lactate level extraction and processing algorithm configured to be running in the memory 220 controlled by the processor 210, utilizes receiving, from a wearable sensor, current lactate level information of a user; setting, by the user, a target fatigue value; determining target lactate level information based on the target fatigue value; receiving characteristics of a physical exercise comprising information of an end of the physical exercise; determining adjusted characteristics of the physical exercise in order to match the current user lactate level information in the end of the physical exercise with the target lactate level information, based on the current lactate level information of the user, the target lactate level information and the characteristics for the physical exercise; and providing feedback to the user based on the adjusted characteristics of the physical exercise.

In an embodiment, geographical map information may be downloaded and maintained in the user apparatus memory 220 for tracking and defining a route for the physical exercise. Adjusted characteristics for the physical exercise may then comprise re-routing the exercise (e.g. jogging). Furthermore, the geographical map information may also comprise topography information. The topography information may then be used as a further input for determining adjusted characteristics of the physical exercise in order to match the current user lactate level information in the end of the physical exercise with the target lactate level information. Running uphill is more strenuous and routing over hills will result in a more exhaustive exercise.

Figure 3:
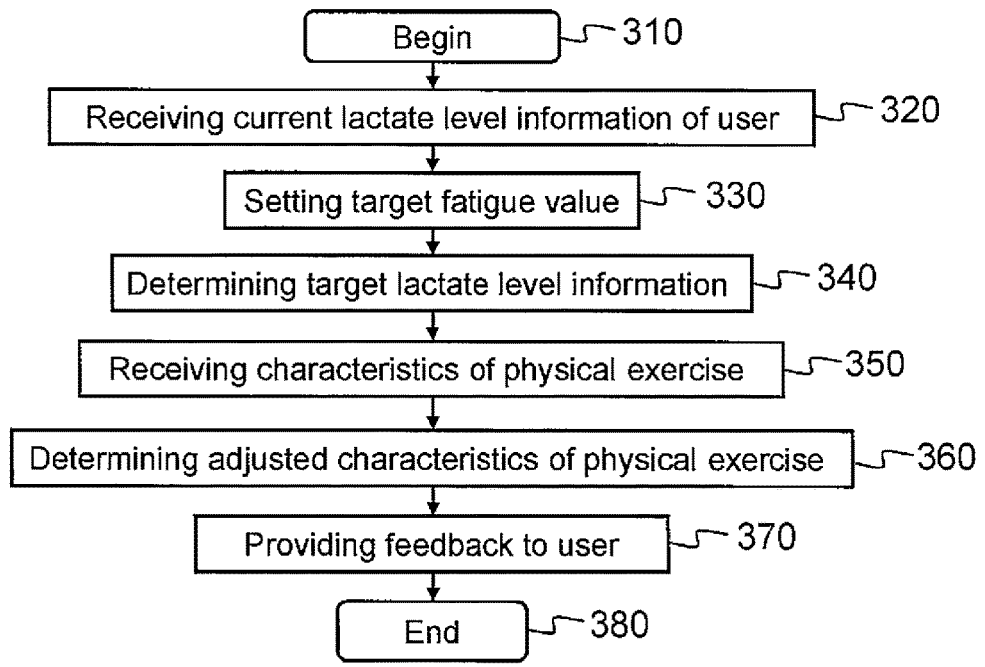
FIG. 3 shows a flow chart of a process of an example embodiment.

FIG. 3 shows a flow diagram illustrating a method according to an example embodiment of the invention. The method begins at step 310. In step 320, current lactate level information of a user is received from a wearable sensor. In step 330, a target fatigue value is set by the user. In step 340, target lactate level information is determined based on the target fatigue value. In step 350, characteristics of a physical exercise are received, comprising information of an end of the physical exercise. In step 360, adjusted characteristics of the physical exercise is determined, in order to match the current user lactate level information in the end of the physical exercise with the target lactate level information, based on the current lactate level information of the user, the target lactate level information and the characteristics for the physical exercise. In step 370, feedback is provided to the user based on the adjusted characteristics of the physical exercise. The method ends at step 380.

Figure 4:
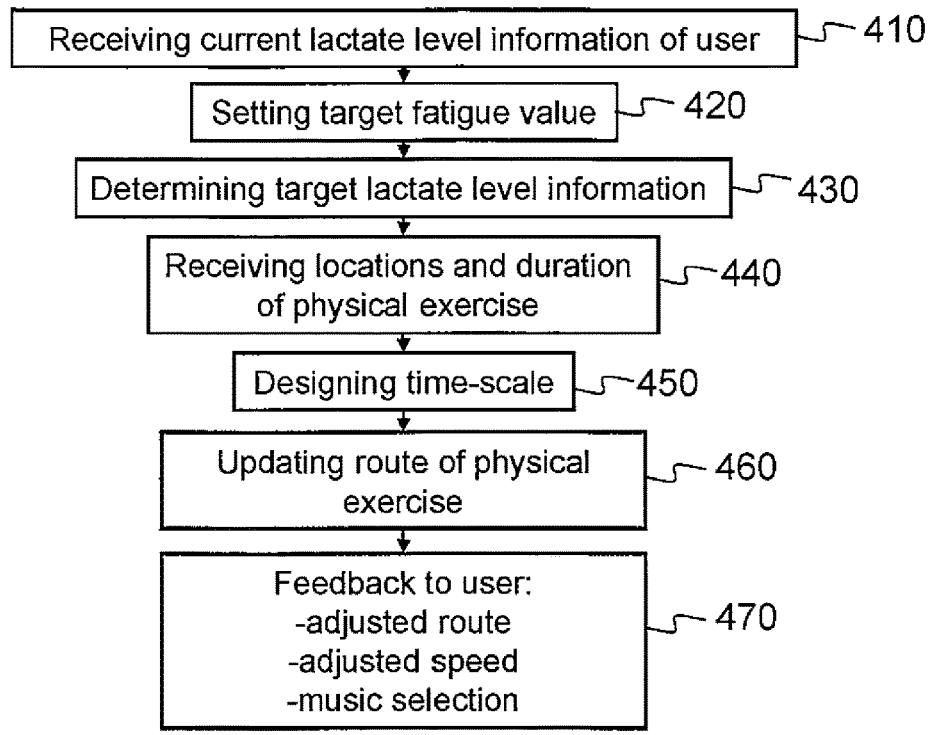
FIG. 4 shows a flow chart of a process according to an example embodiment.

FIG. 4 shows a flow chart of a process according to an example embodiment of the invention.

The process comprises receiving 410, from a wearable sensor, current lactate level information of a user, and setting 420, by the user, a target fatigue value. The target fatigue value may be given, for a fixed duration exercise, by the user to set his desired end exhaustion level measured by lactate acid in his body in the end of the exercise. Based on the target fatigue value, target lactate level information 430 is determined by the apparatus. Alternatively, the user may give directly the target lactate level information, if desired, and then the target fatigue value is not needed.

The process further comprises receiving characteristics of physical exercise 440 comprising information of beginning and end locations of the physical exercise, as well as duration for the exercise, set by the user.

The process further comprises monitoring the user's lactate (acid) levels and designing a time-scale 450, where the lactate acid-levels gradually rise from the current levels to finish at the desired exhaustion level. The time-scale length equals the desired exercise duration. In case of jogging, for example, the apparatus makes an estimate of how long a distance the user can run to fit the time-scale and the apparatus maps a fitting course.

The process further comprises determining adjusted characteristics 460 of the physical exercise, in order to match the current user lactate level information in the end of the physical exercise, with the target lactate level information, based on the current lactate level information of the user, the target lactate level information and the characteristics for the physical exercise. Thus, the process may automatically update the route 460 to fit the plan better by making adjustments to the route for jogging. Topography information available, for example, from map information of the area for the physical exercise may be used when re-routing.

Furthermore, the process comprises providing feedback to the user based on the adjusted characteristics of the physical exercise. Such feedback 470 may comprise instructions on the updated route 460, and informing the user how fast to go in order to achieve the end exhaustion level. In an embodiment, the process comprises playing faster music if the lactate (acid) levels fall sort of the plan during the exercise, and playing slower music if the lactate (acid) levels are above the plan.

The feedback 470 may also comprise at least one of the following:

Text-to-speech feedback provided by the user apparatus 120, for example "run faster!" or "slow down!".

Beeps provided by the user apparatus 120 indicating a needed change in the physical exercise, and further directive may be provided to the user on the user interface as a text or graphics, for example.

Figure 5:
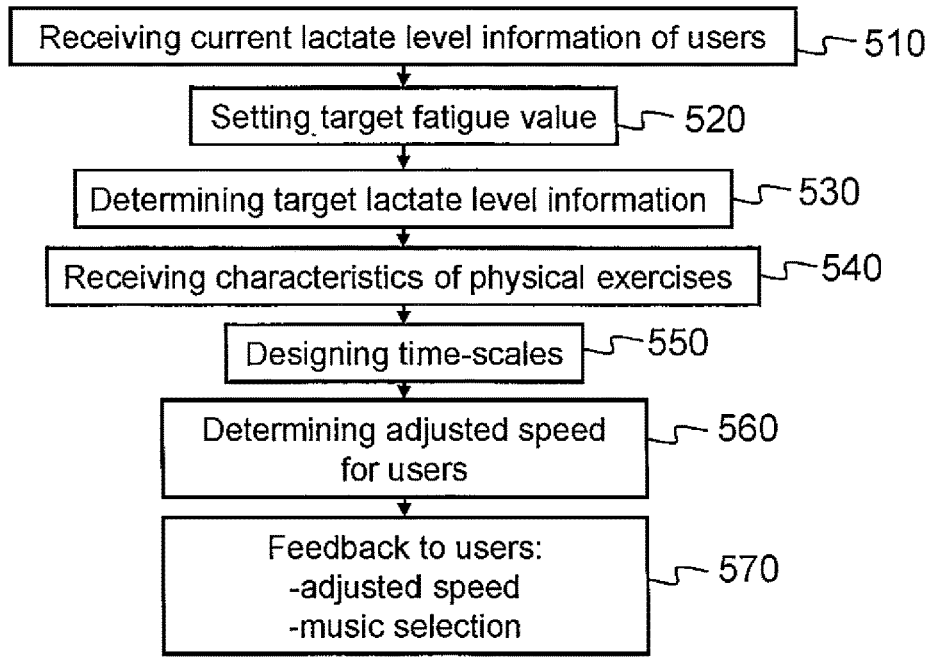
FIG. 5 shows a flow chart of a process according to another example embodiment.

FIG. 5 shows a flow chart of a process according to another example embodiment of the invention. Different training programs may be defined for people who are training together but who are in different physical conditions.

The process comprises receiving 510, from a first wearable sensor, current lactate level information of a first user, and from a second wearable sensor, current lactate level information of a second user.

The process further comprises setting 520, by at least one of the users, a target fatigue value. The target fatigue value may be given, for a fixed duration exercise, by the users to set the desired end exhaustion level measured by lactate acid in their body in the end of the exercises. Based on the target fatigue value, target lactate level information 530 is determined by at least one user apparatus for both users. Alternatively, the users may give exact target lactate level information, if desired.

Then, characteristics of a first and a second physical exercise are received 540 comprising information of an end of the first and the second physical exercise. For example, the at least two users may be using a running mill or a spinning device, and want to have an equal duration exercise and to be equally tired at the end of it, even though they are physically in different conditions. Both have devices with lactate (acid) level sensors. The device monitors the user's lactate (acid) levels and aim to have the same level at the end of the exercise. In such case the characteristics comprise information of an end time of the first and the second physical exercise.

The process further comprises monitoring the user's lactate (acid) levels and designing time-scales 550 where the lactate acid levels of multiple users gradually rise from the current levels to finish at the desired exhaustion level. The time-scale length equals the desired exercise duration.

The process further comprises determining adjusted characteristics of the first and second physical exercise, in order to match the current user lactate level information of the second user in the end of the second physical exercise, with the target lactate level information of the first user, based on the current user lactate level information of the second user, the target lactate level information of the first user and the characteristics for the second physical exercise. The adjusted characteristics may comprise, for example, adjusted speeds 560 for the first and the second user based on the time-scales 550.

Furthermore, feedback 570 to the first and the second user is provided based on the adjusted speed of the physical exercise. If one user falls short of the planned lactate (acid) levels during the exercise, the apparatus plays him faster music and vice versa.

Figure 6:
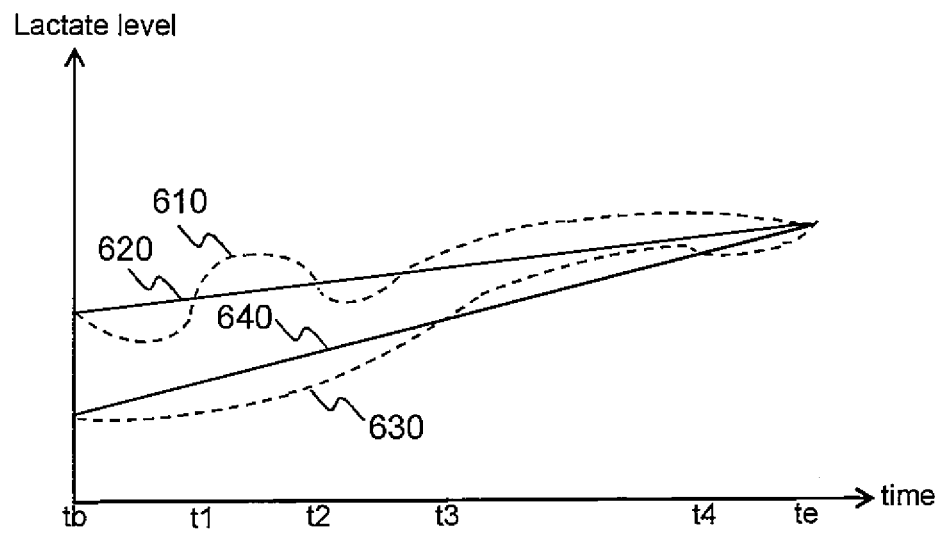
FIG. 6 shows a schematic illustration of current lactate levels and planned (time-scale) lactate levels of a first and a second user according to an embodiment.

FIG. 6 shows a schematic illustration of current lactate levels and planned (time-scale) lactate levels of a first and a second user according to an embodiment disclosed relating to FIG. 5.

At time tb, physical exercises for both users begin. As can be seen in FIG. 6, a lactate level 610 of the first user at the beginning (time=tb) may be higher than a lactate level 630 of the second user. Planned lactate levels 620, 640 for the first and the second user, respectively, are determined to be at the same level at the end (time=te) of the physical exercises, corresponding to a situation where both users are equally exhausted in the end (similar fatigue value). Lactate levels 610, 630 are determined based on the received lactate level information from the user wearable lactate level sensors.

In an embodiment, between tb and t1, as can be seen from FIG. 6, the current lactate level 610 of the first user is below the planned lactate level 620 and feedback comprising faster music (quicker tempo), for example, is provided to the first user in order to increase the measured lactate level 610 in view of the planned level 620. Correspondingly, between t1 and t2, as can be seen from FIG. 6, the current lactate level 610 of the first user is above the planned lactate level 620, and feedback comprising slower music (slower tempo), for example, is provided to the first user in order to decrease the measured lactate level 610 in view of the planned level 620. Then again, between tb and t3, the current lactate level 630 of the second user is below the planned lactate level 640 and feedback comprising faster music is provided to the second user, in order to increase the measured lactate level 630 in view of the planned level 640. Correspondingly, between t3 and t4, the current lactate level 630 of the second user is above the planned lactate level 640, and feedback comprising slower music is provided to the second user in order to decrease the measure lactate level 630 in view of the planned level 640. Eventually, at the end of the exercise (time=te) the measured current lactate levels 610, 630 match for the first and the second user.

In an embodiment, two users may want to go for example jogging outdoors. The users may have very different physical conditions and thus require different exercises to reach similar fatigue in the end. A first user may require 20 km run in one hour to get tired and a second user suffices with 10 km within the hour. User apparatuses of the two users may be synchronized/paired to provide similar exhaustion levels at the end of the jogging, as is illustrated in FIG. 6 and embodiments disclosed. Routes for both users may be determined, as well as suitable speeds. However, instead of reaching the same exhaustion level in the end of the exercise, (time=te), the target moment when the measured current lactate levels 610, 630 match for the first and the second user may be determined to be slightly earlier, for example at time=t4 in FIG. 6. Furthermore, the routes for the first and second users may be defined so that at time=t4 both users end up to the same location (for example a crossroads or other waypoint). The first and the second user may then end the training by walking or slowly jogging the final part of the route together and start a recovering process for their exercises.

Figure 7:
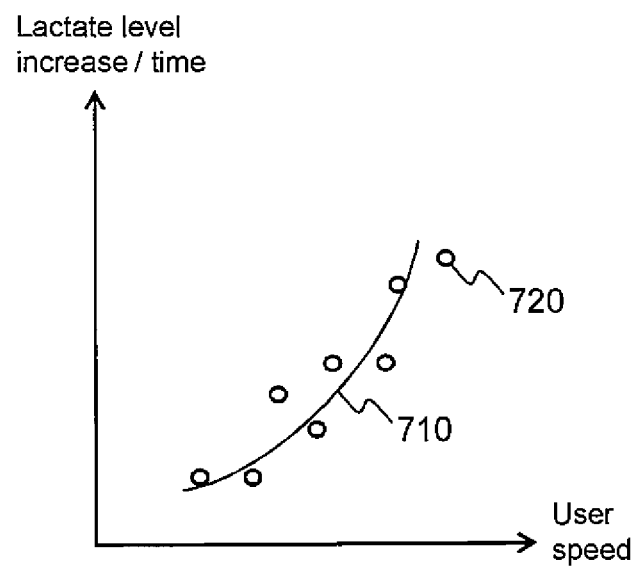
FIG. 7 shows a schematic illustration of a process according to another embodiment, wherein the process comprises monitoring, during the physical exercise, user lactate level information and a user speed; and defining, using the monitored user lactate level information and the user speed, a model of the user lactate level information as a function of the speed.

FIG. 7 shows a schematic illustration of a process according to another embodiment, wherein the process comprises monitoring, during the physical exercise, user lactate level information and a user speed; and defining, using the monitored user lactate level information and the user speed, a model of the user lactate level information as a function of the speed.

In an embodiment, the model may be a polynomial regression model, and the process further comprises monitoring user lactate level information and a user speed during pre-determined time periods; determining average speed and user lactate level increase for the time periods; defining the polynomial regression model having a polynomial order of two using the average speed and the user lactate level increase for the time periods; determining an estimate of a remaining duration of the physical exercise based on the end location of the predetermined route and the adjusted speed; and selecting a music file of a duration similar to the remaining duration of the physical exercise. Other models and other polynomial model orders may be used depending on the user and characteristics of the physical exercise, for example.

In an embodiment, the process further comprises maintaining history data of earlier monitored user lactate level information and user speeds; and defining, using the history data, a model of the user lactate level information as a function of the speed.

User may, for example, set a course for a running/cycling exercise and a desired exhaustion level (fatigue value) in the end of the exercise. During the exercise the system monitors the user lactate (acid) levels and makes a model of how the levels build as a function of the speed of the user. One method of doing this is to measure speed and lactate (acid) level increases over short time periods, and to calculate average speed and lactate (acid) level increase within the periods to provide measured data 720, and then fit a polynomial using polynomial regression 710 to the measured data 720, as illustrated in FIG. 7. The system may also use previously measured data maintained as history data within the apparatus or in the server.

In an embodiment, a second order polynomial 710 is fitted to measured data 720. Other order polynomials and other fitting methods may be used too. In an embodiment, the polynomial is assumed to be following:

$$l = av^2 + bv + c$$

Terms a, b, and c are parameters that fit the polynomial to the measured data 720 (using the polynomial regression method), v is the speed of the user and l is the lactate (acid) level increase per second at this speed.

User desired exhaustion level at the end of the physical exercise is measured as the amount of lactate acid. User desired end level may be notated as $l\_f$, current level as $l\_c$, and time from present to the end of the physical exercise as t. In order to achieve the desired exhaustion level at the end of the exercise, following equation may be defined during the exercise:

$$l_c + lt = l_f$$

Above assumes that a constant exercise level is kept during the remainder of the exercise. Since in practice the exercise level changes, these equations need to be constantly updated during the exercise. For example, even if the user speed is the same, the exercise difficulty may change when you are going uphill or downhill. Similarly, training in thin air affects the difficulty.

Furthermore, by using s to notate the remaining distance of the physical exercise and its course, and using the two equations above, we get:

$$v = \frac{l_f - l_c - bs \pm \sqrt{(l_f - l_c - bs)^2 - 4acs^2}}{2as}$$

Above equation results with two solutions, a positive and a negative solution. The positive speed v is selected. The equation means that the user should aim for target speed v during the physical exercise in order to achieve the desired exhaustion level in the end of the physical exercise. The value of v should be constantly updated during the physical exercise.

In an embodiment, instead of speed, a general level of exercise exhaustiveness may be used because in some physical exercises the user may not move much.

In an embodiment, the process further comprises playing faster music if the user falls behind the target speed, or slower music if the user is faster than the target speed. Alternatively, the system may use other means to tell the user that he should change his speed, such as visual information, audio information of tactile feedback, for example.

Using the defined speed value v, also the expected remaining time of the physical exercise can be calculated:

$$t = \frac{s}{v}$$

In an embodiment, the process further comprises selecting music from a music library for the user so that the rhythm of the music makes the user run at the right speed, and also so that the last song played for the user ends at the expected end time of the physical exercise, which is calculated above.

Figure 8:
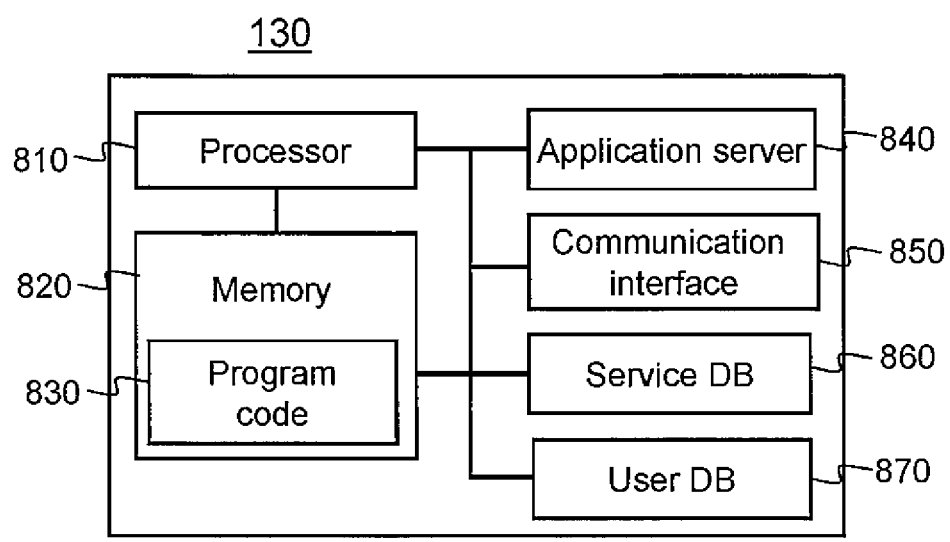
FIG. 8 shows a block diagram of a server apparatus of an example embodiment.

FIG. 8 shows a block diagram of a server apparatus of an example embodiment.

The general structure of the server apparatus 130 comprises a processor 810, and a memory 820 coupled to the processor 810. The server apparatus 130 further comprises software 830 stored in the memory 820 and operable to be loaded into and executed in the processor 810. The software 830 may comprise one or more software modules and can be in the form of a computer program product.

The processor 810 may be, e.g., a central processing unit (CPU), a microprocessor, a digital signal processor (DSP), a graphics processing unit, or the like. FIG. 8 shows one processor 810, but the server apparatus 130 may comprise a plurality of processors.

The memory 820 may be for example a non-volatile or a volatile memory, such as a read-only memory (ROM), a programmable read-only memory (PROM), erasable programmable read-only memory (EPROM), a random-access memory (RAM), a flash memory, a data disk, an optical storage, a magnetic storage, a smart card, or the like. The server apparatus 130 may comprise a plurality of memories. The memory 820 may be constructed as a part of the server apparatus 130 or it may be inserted into a slot, port, or the like of the server apparatus 130 by a user. The memory 820 may serve the sole purpose of storing data, or it may be constructed as a part of an apparatus serving other purposes, such as processing data.

The communication interface module 850 implements at least part of data transmission. The communication interface module 850 may comprise, e.g., a wireless or a wired interface module. The wireless interface may comprise such as a WLAN, Bluetooth, infrared (IR), radio frequency identification (RF ID), GSMIGPRS, CDMA, WCDMA, or LTE (Long Term Evolution) radio module. The wired interface may comprise such as Ethernet or universal serial bus (USB), for example. The communication interface module 850 may be integrated into the server apparatus 130, or into an adapter, card or the like that may be inserted into a suitable slot or port of the server apparatus 130. The communication interface module 850 may support one radio interface technology or a plurality of technologies. Configuration information between the user apparatus 120 and the system server 130 may be transceived using the communication interface 850. Similarly, account creation information between the system server 130 and a service provider may be transceived using the communication interface 850.

An application server 840 provides application services e.g. relating to the user accounts stored in a user database 870 and to the service information stored in a service database 860. The service information may comprise content information, content management information or metrics information, for example. The service information may also comprise information relating to current lactate level information of a user, target fatigue value, target lactate level information mappings to target fatigue values, characteristics of physical exercises, adjusted characteristics of physical exercises, music library to be used for feedback, history data of earlier monitored user lactate level information and user speeds; models of the user lactate level information as a function of the speed, and route information of earlier exercises, for example.

A skilled person appreciates that in addition to the elements shown in FIG. 8, the server apparatus 130 may comprise other elements, such as microphones, displays, as well as additional circuitry such as input/output (I/O) circuitry, memory chips, application-specific integrated circuits (ASIC), processing circuitry for specific purposes such as source coding/decoding circuitry, channel coding/decoding circuitry, ciphering/deciphering circuitry, and the like.

Without in any way limiting the scope, interpretation, or application of the claims appearing below, a technical effect of one or more of the example embodiments disclosed herein is improved method and apparatus for physical exercise control. Another technical effect of one or more of the example embodiments disclosed herein is improved determination of lactate level information of a user during a physical exercise, estimating desired lactate level and providing more accurate feedback to user for reaching the desired lactate level. Another technical effect of one or more of the example embodiments disclosed herein is that a plurality of users with different physical condition may train together with similar exhaustion level at the end of the exercise. Another technical effect of one or more of the example embodiments disclosed herein is that no complex measurement apparatus is needed, and non-invasive biometric sensors may be used to provide more simple system.

If desired, the different functions discussed herein may be performed in a different order and/or concurrently with each other. Furthermore, if desired, one or more of the before-described functions may be optional or may be combined.

Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while the foregoing describes example embodiments of the invention, these descriptions should not be viewed in a limiting sense. Rather, there are several variations and modifications, which may be made without departing from the scope of the present invention as defined in the appended claims.

The invention claimed is:

1. A method, comprising:
   receiving, from a wearable sensor, current lactate level information of a user performing physical exercise;
   setting, by the user, a target fatigue value for the physical exercise;
   determining with a lactate level extraction and processing method target lactate level information based on the target fatigue value;
   receiving characteristics of the physical exercise comprising information of an end exhaustion level of the physical exercise measured by lactate acid in a body of the user during the physical exercise;
   determining adjusted characteristics comprising adjustments to at least one of a route and a speed of the physical exercise in order to match the current user lactate level information in the end of the physical exercise with the target lactate level information, based on the current lactate level information of the user, the target lactate level information and the characteristics for the physical exercise; and
   outputting feedback comprising an indication of the adjusted characteristics of the physical exercise causing the user to adjust the at least one of a route and a speed of the physical exercise based on the adjusted characteristics.

2. The method of claim 1, further comprising:
   wherein the characteristics of the physical exercise comprise information of a start time, a start location, an end time, and an end location of the physical exercise; the method further comprising:
   defining a time-scale for lactate level information, wherein lactate levels gradually rising from the current lactate level to a target lactate level, and a time-scale length determined based on the start time and the end time of the physical exercise;
   estimating a distance covered by the user during the physical exercise to match the time-scale;
   determining route information between the start location and the end location based on the estimated distance; and
   outputting feedback to the user comprising instructions based on the route information.

3. The method of claim 2, further comprising:
   dynamically estimating a distance covered by the user during the physical exercise to match the time-scale;
   updating route information between the start location and the end location based on the estimated distance; and
   outputting feedback to the user comprising instructions based on the updated route information.

4. The method of claim 2, further comprising:
   comparing the current lactate level information to the defined time-scale for lactate level information; and
   outputting feedback comprising a music file with a higher tempo in response to the current lactate level information being below the defined time-scale, based on the comparison; and
   outputting feedback comprising a music file with a lower tempo in response to the current lactate level information being above the defined time-scale, based on the comparison.

5. The method of claim 1, further comprising;
   receiving, from a second wearable sensor, current lactate level information of a second user;
   receiving characteristics of a second physical exercise comprising information of an end of the second physical exercise;
   determining adjusted characteristics of the second physical exercise in order to match the current user lactate level information of the second user in the end of the second physical exercise with the target lactate level information of the first user, based on the current user lactate level information of the second user, the target lactate level information of the first user and the characteristics for the second physical exercise; and
   outputting feedback based on the adjusted characteristics of the second physical exercise to the second user.

6. The method of claim 1, wherein the information of an end of the physical exercise comprising an end location of a predetermined route, the adjusted characteristics of the physical exercise comprising an adjusted speed for the physical exercise following the predetermined route, and the feedback to the user comprising instructions to change exercise speed based on the adjusted speed, and the method further comprising:
   determining an estimate of a remaining duration of the physical exercise based on the end location of the predetermined route and the adjusted speed; and
   selecting a music file of duration similar to the remaining duration of the physical exercise.

7. The method of claim 1, wherein the physical exercise comprising at least one of the following:
   walking;
   jogging;
   skating;
   cross-country-skiing;
   running;
   swimming; and
   cycling.

8. The method of claim 1, further comprising:
   monitoring, during the physical exercise, user lactate level information and a user speed; and
   defining, using the monitored user lactate level information and the user speed, a model of the user lactate level information as a function of the speed.

9. The method of claim 8, wherein the model being a polynomial regression model, and the method further comprising:
   monitoring user lactate level information and a user speed during pre-determined time periods; determining average speed and user lactate level increase for the time periods;

defining the polynomial regression model having a polynomial order of two using the average speed and the user lactate level increase for the time periods;
determining an estimate of a remaining duration of the physical exercise, based on the end location of the predetermined route and the adjusted speed; and
selecting a music file of duration similar to the remaining duration of the physical exercise.

10. The method of claim 8, further comprising:
maintaining history data of earlier monitored user lactate level information and user speeds; and
defining, using the history data, a model of the user lactate level information as a function of the speed.

11. The method of claim 1, wherein the lactate level extraction and processing method is using a lactate level extraction and processing algorithm.

12. An apparatus comprising:
a user interface for transceiving information with a user;
at least one memory including computer program code;
the at least one memory and the computer program code configured to, with the at least one processor, cause the apparatus to:
receive current lactate level information of a user; set, by the user, a target fatigue value;
determine with a lactate level extraction and processing method target lactate level information based on the target fatigue value;
receive characteristics of a physical exercise comprising information of an end exhaustion level of the physical exercise measured by lactate acid in a body of the user during the physical exercise;
determine adjusted characteristics comprising adjustments to at least one of a route and a speed of the physical exercise in order to match the current user lactate level information in the end of the physical exercise with the target lactate level information, based on the current lactate level information of the user, the target lactate level information and the characteristics for the physical exercise; and
output feedback comprising an indication of the adjusted characteristics of the physical exercise causing the user to adjust the at least one of a route and a speed of the physical exercise based on the adjusted characteristics.

13. The apparatus of claim 12, comprising the wearable sensor, wherein the apparatus is a user wearable apparatus.

14. The apparatus of claim 12, further comprising:
a communication interface for receiving biometric non-invasive information from a wearable sensor, wherein the at least one memory and the computer program code further configured to, with the at least one processor, cause the apparatus to:
process the received biometric non-invasive information to provide current lactate level information of a user.

15. A computer program embodied on a non-transitory computer readable medium comprising computer executable program code configured to control an apparatus, when the computer executable program code is executed, to:
receive current lactate level information of a user;
set, by the user, a target fatigue value;
determine with a lactate level extraction and processing method target lactate level information based on the target fatigue value;
receive characteristics of a physical exercise comprising information of an end exhaustion level of the physical exercise measured by lactate acid in a body of the user during the physical exercise; and
determine adjusted characteristics comprising adjustments to at least one of a route and a speed of the physical exercise in order to match the current user lactate level information in the end of the physical exercise with the target lactate level information, based on the current lactate level information of the user, the target lactate level information and the characteristics for the physical exercise; and
output feedback the adjusted characteristics of the physical exercise causing the user to adjust the at least one of a route and a speed of the physical exercise based on the adjusted characteristics.

* * * * *